United States Patent [19]

Lewis

[11] 4,330,507

[45] May 18, 1982

[54] METHOD AND SYSTEM FOR GENERATING AND COLLECTING GALLIUM-68 USING ALKALINE ELUANT

[75] Inventor: Robert E. Lewis, Milford, N.H.

[73] Assignee: New England Nuclear Corporation, Boston, Mass.

[21] Appl. No.: 158,395

[22] Filed: Jun. 11, 1980

[51] Int. Cl.[3] ..................... G01N 23/12; C01G 15/00; A61K 43/00; A61K 49/00

[52] U.S. Cl. ................................. 423/2; 250/432 PD; 424/1

[58] Field of Search ................ 252/645; 423/2; 424/1; 250/432 PD

[56] References Cited

U.S. PATENT DOCUMENTS

| | | | |
|---|---|---|---|
| 4,224,303 | 9/1980 | Shaw | 424/1 |
| 4,248,730 | 3/1981 | Mirzadeh et al. | 423/2 |
| 4,264,468 | 4/1981 | Neiri nckx et al. | 424/1 |

OTHER PUBLICATIONS

Malyshev et al., Soviet Radiokhimiya, 17:137–139 (1975).

Seidl et al., Radiochem, Acta, 12:196–198 (1978).

Kopecky et al., Int. J. Appl. Rad. Isot., 25:263–268 (1974).

Ehrhardt et al., J. Nucl. Med., 19:925–929 (1978).

Gleason, Int. J. Appl. Rad. Isot. 8:90–94 (1960).

Galetka et al., J. Radio Anal. Chem., 21:349–353 (1974).

Kopecky et al., Int. J. Appl. Rad. Isot., 24:73–80 (1973).

Neirinckx et al., "The Radio Pharm. Sc. Council 2nd Int. Symp. on Radiopharm.," Seattle, Wash., (1979).

Iofa et al., Soviet Radiokhimiga, 12:770 (1970).

Greene et al., Int. J. Appl. Rad. Isot., 12:62 (1961).

*Primary Examiner*—Christine M. Nucker

*Attorney, Agent, or Firm*—Sewall P. Bronstein; George W. Neuner

[57] ABSTRACT

A method for generating Ga-68 from Ge-68 is provided that comprises contacting a substrate on which Ge-68 has been adsorbed with an alkaline solution having a pH of at least about 12 and thereby eluting Ga-68. Preferably the Ga-68 is eluted in the form of the gallate ion. A generator system comprises a generator column containing Ge-68 and Ga-68, a sealed eluant container having a predetermined quantity of eluant comprising an alkaline solution having a pH of at least about 12, and an evacuated eluate collection vial having a vacuum sufficient to draw the desired quantity of eluate into the eluate collection vial. The eluate collection vial can contain a neutralizing agent and also a diagnostically useful complexing agent.

19 Claims, No Drawings

METHOD AND SYSTEM FOR GENERATING AND COLLECTING GALLIUM-68 USING ALKALINE ELUANT

FIELD OF THE INVENTION

This invention relates to the generation of Ga-68 from Ge-68 and the collection of Ga-68 by elution from ion exchange material containing the Ge-68, and particularly to a method and system for eluting the Ga-68 in strongly basic eluant solutions preferably having a pH of 12 or greater.

BACKGROUND OF THE INVENTION

Generators of short lived radionuclides are widely used in nuclear medicine, the most common of which is the Mo-99/Tc-99 m generator. Other parent-daughter radionuclides can also be used for a supply of the short lived daughter, provided the parent and daughter are easily separated and the daughter is readily converted, if necessary, to useful radiopharmaceutical preparations.

Gallium radioisotopes, in particular Ga-67, have been used extensively for imaging tumors and abscesses by gamma scintigraphy. The chemistry of ionic gallium in the body has been well studied. There has been considerable interest in the Ge-68/Ga-68 generator as a source of Ga-68. The 287 day half-life Ge-68 parent decays to the positron emitting 68 minute half-life Ga-68.

Since their development, positron-imaging devices have been used in a variety of studies employing positron-emitting radionuclides, the most advanced utilizing tomographic techniques. Gallium-68 is also well-suited for such positron tomography. The high resolving power of positron tomagraphy reduces the need for sophisticated collimators as well as a high target to non-target ratio, compared with that required for gamma scintigraphy using Ga-67.

The first isolation of Ga-68 was disclosed by G. I. Gleason, *Int. J. Appl. Radiat. Isotopes,* 8,90 (1960) and required that Ga-68 be separated from its parent by solvent extraction. The activity was back extracted into dilute HCl from which the injectable preparation was made. A similar type separation using acetylacetone-carbon tetrachloride for solvent extraction separation was described by Iofa et al., *Radiokhimiya,* 12, 796 (1970). An improved generator was described by Greene et al., *Int. J. Appl. Radiat. Isotopes,* 12, 62 (1961) in which the parent Ge-68 was loaded on an activated alumina column and the Ga-68 was eluted with an 0.005 M solution of ethylenediaminetetraacetic acid (EDTA), previously adjusted to pH 7 with sodium hydroxide.

Generators based upon adsorption and extraction columns, like those described by Greene et al., have been preferred over liquid generators, from which the desired daughter-radionuclide must be extracted by liquid phase separation techniques, because the column type generators are more convenient and can be operated by persons having less experience and less skill.

The preparation of Ge-68/Ga-68 adsorption and extraction generators have been described by many authors, and this adsorbant substrate type generator has been commercially available for several years. Ga-68 is eluted from it with 0.005 M EDTA solution as a Ga-68 EDTA complex. Nevertheless, for most applications it is necessary to use preparations containing Ga-68 in an ionic form. Because gallium-68 is obtained by elution of a Ge-68/Ga-68 generator with EDTA solution, the gallium is present in the eluate as gallium-EDTA chelate and must be chemically separated from the EDTA prior to its use as a label.

Thus, several disadvantages of the column type Ga-68 generators using complexing agents were set forth by Ehrhardt et al., *J. Nucl. Med.,* 19 (8), 925–29 (1978) as follows. Elution at neutral pH over the long useful life of the generator causes difficulty in maintaining generator sterility. Secondly, Ga-68 can be produced by present generators only as the EDTA complex. Preparation of radiopharmaceuticals other than Ga-EDTA requires decomposition of the complex and removal of virtually all the EDTA in order for weaker complexing agents to bind successfully with the gallium. The decomposition of Ga-EDTA requires subsequent solvent extraction, ion exchange, or pyrolysis all of which are tedious and time-consuming when speed is essential. Furthermore, Ehrhardt et al. (ibid.) state that it is doubtful whether these methods can produce radiopharmaceuticals uncontaminated by Ga-EDTA, since even quantities of EDTA as small as $10^{-18}$ moles in competition with chelates having a stability constant of $\log K \simeq 10$ can lead to Ga-68 preparations that are $\sim 10\%$ Ga-68 EDTA, due to the very high stability constant of Ga-EDTA ($\log K = 34$).

Thus, Ehrhardt et al. suggest a solvent system using a weaker complex that EDTA for recovery of Ga-68 from the germanium, and suggest extracting the Ga-68 with oxine in chloroform followed by conversion of this Ga complex to other radiopharmaceutical forms. This procedure is similar to the solvent extraction procedures of Gleason and Iofa et al., mentioned previously.

Because of the desirability of obtaining ionic forms of Ga-68 instead of complexes such as EDTA, procedures for separating Ga-68 from EDTA solutions were developed. However, it remains highly desirable to obtain the ionic Ga-68 directly from a column type generator. Seidl et al., *Radiochim. Acta.,* 19, 196–8 (1973) describe a Ga-68 generator using hydrous zirconium oxide as the adsorbant and 0.1 N HCl for elution. However, the yield of Ga-68 was only 5%, too low to be of practical use. Higher Ga-68 yields were found with 0.1 N $HNO_3$, but these solutions were not useful for medical preparations. Another generator using zirconium hydroxide as the adsorbant was disclosed by Malyshev et al., *Radiokhimiya,* 17(1), 137–40 (1975) in which the yield of Ga-68 was 35% with Ge-68 impurity from $3\times10^{-2}$ to $6\times10^{-3}\%$.

Another approach described by Caletka et al., *J. Radioanalytical Chem.,* 21, 349 (1974) was to sorb $GeCl_4$ on silica gel, and elute the Ga-68 with 8–10 N HCl. Yields were good, but the eluate required subsequent processing to remove the excess HCl.

A generator described by Kopecky et al., *Int. J. Appl. Radiat. Isotopes,* 24, 73–80 (1973) and Kopecky et al., *Int. J. Radiat. Isotopes,* 25, 263–68 (1974) using alumina and eluted with 0.1 through 0.2 N HCl yielded about 30 to 65% Ga-68. The gallium obtained from such a generator is ionic and can be made into numerous radiopharmaceuticals. The main disadvantage of this generator is that the $Al^{+3}$ content of the eluate is about 10–18 ppm for a 1.5 g alumina column, and may vary considerably with the source of the alumina. Also on aging, yields of Ga-68 decrease or are variable for the HCl-alumina system.

Ga-68 generator systems using organic ion exchangers have been described by Neirinckx et al., 2nd International Symposium on Radiopharmaceuticals, The Radiopharmaceutical Science Council, Mar. 18, 1979 (Seattle, Washington). A disadvantage of such generators is that organic resins may decompose in high radiation fields.

Most of the generators described in the literature have been 0.1 μCi to a maximum of 0.3 mCi Ge-68/Ga-68. At these levels suitable organic resins might be used, but at practical levels of 1–100 mCi Ge-68, radiation effects over the life of the generator can affect the organic resins, giving degradation products in the Ga-68 eluate which may be undesirable for medical use.

Thus, a simple and efficient generator system for obtaining Ga-68 in ionic form is quite desirable and would afford significant benefit to the field of nuclear medicine.

SUMMARY OF THE INVENTION

In accord with the present invention Ga-68 is eluted directly from a Ge-68/Ga-68 generator, in which Ge-68 is adsorbed on a solid substrate, by contacting the substrate with a solution having a pH of at least about 12. Suitable as eluants are sodium hydroxide and sodium phosphate solutions.

In a preferred embodiment, the present invention provides an adsorbant substrate type Ge-68/Ga-68 generator and method for elution of a Ga-68 in which the $^{68}GaO_2^-$ ion (gallate) is obtained. The advantage of $GaO_2^-$ is that on treatment with acids $Ga^{+3}$ is formed.

$$GaO_2^- + 4H^+ \rightarrow Ga^{+3} + 2H_2O$$

The $Ga^{+3}$ form of gallium is readily converted to other forms for use as radiopharmaceuticals.

Preferred Ge-68/Ga-68 generators in accord with this invention comprise a generator column containing Ge-68 and Ga-68, a sealed eluant container having a predetermined quantity of eluant comprising an alkaline solution having a pH of at least about 12, and a pre-evacuated eluate container having a vacuum at least sufficient to draw the desired quantity of eluate into the eluate container.

DETAILED DESCRIPTION OF THE INVENTION

In one embodiment of the invention, a Ga-68 generator system is provided that is capable of providing Gallium-68 in ionic form directly, i.e. without any complex separation or extraction steps. One such system comprises a generator column containing parent Ge-68 and daughter Ga-68, a sealed eluant vial containing a predetermined quantity of eluant comprising a solution having a pH of at least about 12, and a pre-evacuated eluate collection vial having a vacuum at least sufficient to draw the desired quantity of eluate into the eluate vial. Another such system provides the entire supply of eluant for the life of the generator as an integral unit within the generator housing. The physical construction of these generators, their flow diagrams, and their operation have been described extensively in the literature and will be readily apparent to those skilled in the art. Such generators are described in further detail in U.S. Pat. Nos. 3,774,035 and 3,576,998, which are hereby incorporated by reference.

The generator column comprises a bed of ion exchange material that is preferably of alumina, although zirconium oxide or other suitable materials can be used. The Ge-68 is loaded onto the alumina using standard procedures; however, no EDTA is used in the loading solution because it is desired to obtain Ga-68 from this generator that is not complexed with EDTA and any residual EDTA would result in undesired Ga-68-EDTA complexes. Preferably the Ge-68 is loaded on the first ¼ of the alumina column, and the remainder of the alumina bed serves to reduce leakage of the Ge-68 during elution. After adsorbing the Ge-68 on the alumina, the alumina is eluted with a quantity of eluting solution to reduce the leakage of Ge-68 and the generator is ready for use. Preferably the Ge-68 is loaded on the alumina from a solution having a pH in the range of about 7.0 to 8.0.

In use, an eluant container is attached to one end of the generator column. The eluant container can be a vial containing a sufficient quantity of eluant for one elution or it can be a large container having sufficient eluant for as much as the entire useful life of the generator. When the container has sufficient eluant for the life of the generator, the container is preferably a watertight collapsible container such as a polymeric bag. A sealed eluate collection vial having a vacuum is attached to the other end of the generator column, normally by piercing an elastomeric closure. The eluate collection vial has at least a sufficient vacuum to draw a desired quantity of eluant through the generator column and into the vial, leaving the column wet. The eluate collection vial can, in addition, contain further vacuum sufficient to empty the generator column and draw a quantity of air through the column to leave the bed damp-dry.

The quantity of eluant to be passed through the generator column for one elution depends upon a number of variables, including the end use of the eluate, the activity of the generator, the particular eluant, etc. Those skilled in the art can readily determine the desired quantity of eluant for the particular circumstances.

The Ge-68/Ga-68 generator in accord with the present invention differs radically from the prior art in that strongly basic solutions are used to elute the Ga-68 from the column, preferably in the form of radioactive $GaO_2^-$ (the gallate ion). The advantage of $GaO_2^-$ is that on treatment with acids, $Ga^{+3}$ is formed. The $Ga^{+3}$ is then readily converted to other forms or complexed for use as radiopharmaceuticals.

In one embodiment of the invention the eluant container comprises eluant solids that are reconstituted by adding sterile water prior to use.

In another embodiment, the pre-evacuated eluate container contains a predetermined quantity of a neutralizing agent to neutralize or buffer the eluate, preferably at physiological pH. The eluate container may also contain a suitable, diagnostically useful complexing agent or target ligand for the Ga-68 so that it is ready for use. An example of such a useful complexing agent is the citrate ion which also acts as a physiological buffer. Other complexing agents or ligands can be provided depending upon the intended diagnostic use.

Strongly basic eluting solutions, as used herein, means solutions having a pH of at least about 12. The upper limit of the pH of the eluting solution is governed by the amount of Ge-68 leakage and the amount of aluminum ions that can be tolerated in the eluate for the particular application. Preferably, the eluting solution has a pH in the range of about 12 to 13. Suitable alkaline eluting solutions comprise, for instance, 0.1 N NaOH, 0.1 M $Na_3PO_4$, and the like. The sodium phosphate if used, can be with sodium pyrophosphate.

The eluate for most medical applications preferably comprises less than about 0.1% Ge-68 and less than about 20 ppm aluminum. More preferably the eluate comprises less than about 0.06% Ge-68 and less than about 10 ppm aluminum.

The advantages of the present invention will be apparent to those skilled in the art upon reading the above disclosure and the following examples which are provided to further illustrate the invention, but should not be construed to limit it in any way.

EXAMPLE 1

A Ge-68/Ga-68 column having a 2.5 cm long by 0.8 cm diameter bed of alumina as the ion exchange material is prepared in the following manner:

Bio Rad AG-7, (a neutral alumina that has a pH of 8.3–8.5 in water) is used to adsorb Ge-68 at pH 7.0–8.0. The Ge-68 tracer is received as $GeCl_4$ in 0.5 HCl, neutralized to ~pH 7.5, diluted to 0.2 mCi/ml and passed through the alumina at a flow rate of 0.5 to 1.0 ml per minute. The Ge-68 tracer adsorbs on the first 0.6 cm of the alumina column, and the remainder of the alumina bed serves to reduce leakage of the Ge-68 during elution. After adsorbing the Ge-68 on the alumina, the alumina is eluted with 20 ml of 0.1 N NaOH to reduce the leakage of Ge-68 by removal of unbound germanium, and the generator is then ready for use.

EXAMPLE 2

A Ge-68/Ga-68 generator 2.5 cm long by 0.8 cm diameter was prepared in accord with Example 1. Various eluants were used to elute the Ga-68 and the results using 10 ml of eluant are shown in Table 1.

TABLE 1

| Eluant | pH | % $Ga^{68}$ | % $Ge^{68}$ | $Al^{+3}$ leakage (ppm) |
|---|---|---|---|---|
| 1N NaOH | 14 | 64 | 1 | >100 |
| .2N NaOH | 13 | 65 | $6 \times 10^{-2}$ | 15–20 |
| .1N NaOH | 12.6 | 69 | $3 \times 10^{-2}$ | 5–10 |
| .05N NaOH | 12.3 | 33 | $1 \times 10^{-3}$ | <2 |
| .01N NaOH | 12.0 | 10 | $1 \times 10^{-4}$ | <2 |
| 0.1M $Na_3PO_4$ | 12.2 | 60 | $1 \times 10^{-3}$ | 5–10 |
| 0.1M $Na_2CO_3$ | 10.7 | 3 | $<1 \times 10^{-4}$ | <2 |
| 0.1M $NaHCO_3$ | 9.1 | .3 | $<1 \times 10^{-4}$ | <2 |
| 0.15M NaCl | 6.0–8.0 | <.1 | $<1 \times 10^{-4}$ | <2 |
| 0.1M HCl | 1.0 | 14 | 4 | 15–20 |
| .2M HCl | 0.7 | 32 | 15 | 100 |

EXAMPLE 3

Two generators, each ~7.5 mCi Ge-68, were prepared as described in Example 1 and eluted with 5 ml of 0.1 N NaOH approximately once an hour for 1 day, and then 3 times per day for several days. The yield of Ga-68, leakage of Ge-68 and $Al^{+3}$ content of the eluate is shown in Tables 2 and 3. One of these generators, tested over a year later, continued to show excellent results, as indicated in Table 3.

TABLE 2

Elution of Ge-68/Ga-68 Generator
Generator A: 8.44mCi Germanium-68 initially
Generator B: 7.80mCi Germanium-68 initially
Eluant: 5ml of 0.1N Sodium hydroxide

| Generator | mCi Ga-68 | time from previous elution | Percent yield | Leakage µCi Ge-68 | Leakage µCi Ge-68 / mCi Ga-68 | $Al^{+3}$ ppm |
|---|---|---|---|---|---|---|
| A | 4.96 | 24 hr. | 58 | 2.4 | .48 | 5–10 |
| B | 4.70 | 24 hr. | 60 | 1.8 | .38 | 5–10 |
| A | 3.12 | 63 min. | 78 | 2.2 | .70 | 5–10 |

TABLE 2-continued

Elution of Ge-68/Ga-68 Generator
Generator A: 8.44mCi Germanium-68 initially
Generator B: 7.80mCi Germanium-68 initially
Eluant: 5ml of 0.1N Sodium hydroxide

| Generator | mCi Ga-68 | time from previous elution | Percent yield | Leakage µCi Ge-68 | Leakage µCi Ge-68 / mCi Ga-68 | $Al^{+3}$ ppm |
|---|---|---|---|---|---|---|
| B | 2.90 | 61 min. | 79 | 1.2 | .41 | 5–10 |
| A | 2.83 | 65 min. | 67 | 1.9 | .67 | 5–10 |
| B | 2.28 | 62 min. | 62 | 0.8 | .35 | 5–10 |
| A | 3.25 | 102 min. | 60 | 1.3 | .40 | 5–10 |
| B | 2.77 | 100 min. | 55 | 0.7 | .25 | 5–10 |
| A | 2.71 | 67 min. | 64 | 1.3 | .48 | 5–10 |
| B | 2.45 | 67 min. | 63 | 0.6 | .25 | 5–10 |
| A | 2.53 | 60 min. | 64 | 1.1 | .44 | 5–10 |
| B | 2.36 | 60 min. | 64 | 0.6 | .25 | 5–10 |
| A | 2.42 | 60 min. | 61 | 1.0 | .41 | 5–10 |
| B | 2.22 | 60 min. | 60 | 0.5 | .22 | 5–10 |
| A | 4.77 | 22 hr. | 56 | 1.4 | .29 | 5–10 |
| B | 4.32 | 22 hr. | 55 | 0.6 | .14 | 5–10 |
| A | 4.46 | 24 hr. | 53 | 1.2 | .27 | 5–10 |
| B | 4.10 | 24 hr. | 52 | 0.7 | .17 | 5–10 |
| A | 3.85 | 135 min. | 62 | 0.8 | .20 | 5–10 |
| B | 3.54 | 135 min. | 61 | 0.8 | .22 | 5–10 |

TABLE 3

Elution of Ge-68/Ga-68 Generator
Generator A: 8.44mCi Germanium-68 initially
Generator B: 7.80mCi Germanium-68 initially
Eluant: 5ml of 0.1N Sodium Hydroxide

| Generator | mCi Ga-68 | time from previous elution | Percent yield | Leakage µCi Ge-68 | Leakage µCi Ge-68 / mCi Ga-68 | $Al^{+3}$ ppm |
|---|---|---|---|---|---|---|
| A | 2.89 | 4 hr. | 42 | 1.5 | .52 | 5–10 |
| B | 2.74 | 4 hr. | 42 | 1.4 | .51 | 5–10 |
| A | 2.76 | 160 min. | 45 | 1.2 | .43 | 5–10 |
| B | 2.44 | 160 min. | 51 | 0.9 | .36 | 5–10 |
| A | 3.96 | 16 hr. | 53 | 0.6 | .15 | 5–10 |
| B | 3.68 | 16 hr. | 52 | 0.6 | .16 | 5–10 |
| A | 3.37 | 3 hr. | 53 | 0.4 | .11 | 5–10 |
| B | 3.05 | 3 hr. | 51 | 0.6 | .19 | 5–10 |
| A | 3.09 | 170 min. | 49 | 0.6 | .19 | 5–10 |
| B | 2.95 | 170 min. | 51 | 0.6 | .20 | 5–10 |
| A | 4.18 | 16 hr. | 55 | 0.6 | .14 | 5–10 |
| B | 4.04 | 16 hr. | 57 | 0.6 | .14 | 5–10 |
| A | 4.60 | 16 hr. | 60 | 0.6 | .13 | 5–10 |
| B | 3.50 | 16 hr. | 50 | 0.4 | .11 | 5–10 |
| A | 3.20 | 3 hr. | 50 | 0.5 | .15 | 5–10 |
| B | 3.07 | 3 hr. | 51 | 0.5 | .16 | 5–10 |
| A | 3.01 | 3 hr. | 47 | 0.4 | .13 | 5–10 |
| B | 2.92 | 3 hr. | 49 | 0.4 | .13 | 5–10 |
| A | 1.24 | 14 months | 46 | 0.1 | .08 | 10 |
| B | | | Not Tested | | | |
| A | 1.29 | 6 hr. | 48 | 0.1 | .08 | 10 |
| B | | | Not Tested | | | |

Ge-68 leakage can be reduced further by lengthening the alumina bed in the column or by providing a second alumina column. For instance, in an experiment where Ga-68 was eluted with 10 ml of 0.1 N NaOH from a 2.5 cm long bed of alumina and the eluate was passed through a second 2.5 cm long alumina bed, the Ge-68 content of the eluate was reduced from 1.75 µCi (0.05%) to ≦0.1 µCi (0.003%) by the second alumina bed. The Ga-68 yield also decreased from 68% to 62%, with 6% remaining on the second column. Thus, the Ge-68 content of the eluate can be reduced by up to a factor of about 20 with a corresponding loss of about 10% of the Ga-68 with an additional 2.5 cm of alumina bed.

EXAMPLE 4

An 0.375 mCi Ge-68 generator, prepared as described in Example 1, was eluted with 5 ml of 0.1 M sodium phosphate. The sodium phosphate was prepared by adding 5 ml of sterile water to 190 mg of $Na_3PO_4.12H_2O$ in an evacuated 5 ml vial. After dissolution, the eluant had a pH of 12.2 to 12.3.

Elution of the generator gave a 60% yield of Ga-68, with $\leqq$0.01% Ge leakage. The $Al^{+3}$ content of the eluate was ~10 ppm.

EXAMPLE 5

The 0.375 mCi Ge-68 generator described in example 4 was eluted with a mixed solution of sodium orthophosphate and sodium pyrophosphate, using 0.1 M $Na_3PO_4$+0.02 M $Na_4P_2O_7$. This eluant was also effective in eluting Ga-68 with ~60% yield. Eluate from Example 3, 4, and 5 were neutralized with citric acid. The addition of $Na_4P_2O_7$ to the eluant provides an additional benefit: that $Na_4P_2O_7$ complexed the $Al^{+3}$ and prevented $Al(OH)_3$ from precipitating after neutralization of the solution to pH 5–8, whether citric acid was included in the neutralizing solution or not.

The invention has been described in detail along with the preferred embodiments thereof. However, it will be appreciated that those skilled in the art, upon reading this disclosure, may make modifications within the spirit and scope of this invention.

I claim:

1. A method for generating an eluate containing Ga-68 in ionic form, said method comprising contacting an alkaline solution having a pH of at least about 12 with a substrate on which Ge-68 has been adsorbed, thereby eluting Ga-68 in the solution.

2. The method in accord with claim 1 wherein said substrate is alumina and said method further includes loading said substrate with Ge-68 by adsorption from a solution having a pH in the range of from about 7.0 to 8.0.

3. The method in accord with claim 1 wherein the pH of said solution is in the range of about 12 to 13.

4. The method in accord with claim 1 wherein said solution comprises sodium hydroxide.

5. The method in accord with claim 1 wherein said solution comprises sodium phosphate.

6. A Ge-68/Ga-68 generator system for providing Ga-68, said system comprising a generator column containing Ge-68 and Ga-68, a sealed eluant vial containing a predetermined quantity of eluant comprising an alkaline solution having a pH of at least about 12, and an evacuated eluate collection vial having a vacuum at least sufficient to draw the desired quantity of eluate into the eluate collection vial.

7. The generator system in accord with claim 6 wherein said eluant container comprises sufficient eluant for one elution.

8. The generator system in accord with claim 6 wherein said eluant container contains sufficient eluant for the useful life of the generator.

9. The generator system in accord with claim 8 wherein said eluant container comprises a water-tight collapsible container.

10. The generator system in accord with claim 6 wherein said eluate collection vial further contains sufficient vacuum to draw air through the generator column to leave the column bed damp-dry.

11. The system in accord with claim 6 wherein said eluant vial contains sodium hydroxide.

12. The system in accord with claim 6 wherein said eluant vial contains sodium phosphate.

13. The system in accord with claim 6 wherein the solution in said eluant vial is prepared by injecting sterile water into a sealed vial containing a predetermined quantity of eluant solids.

14. The system according to claim 6, including a plurality of said eluant vials and a plurality of said eluate collection vials for a plurality of elutions.

15. The generator system in accord with claim 6 wherein said eluate collection vial further contains a predetermined quantity of a neutralizing agent to neutralize or buffer the eluate.

16. The generator system of claim 15 wherein said eluate collection vial contains a predetermined quantity of diagnostically useful complexing agent for the Ga-68.

17. The generator system of claim 16 wherein said neutralizing agent and said complexing agent is citric acid.

18. A method for generating an eluate containing Ga-68 in non-complexed ionic form, comprising passing a predetermined quantity of eluant from an eluant container through a generator column containing Ge-68 and Ga-68 to form an eluate, and receiving said eluate in a pre-evacuated eluate collection vial having sufficient vacuum to draw said predetermined quantity of eluant through said column and into the eluate collection vial, said eluant comprising an alkaline solution having a pH in the range of from about 12 to 13.

19. The method in accord with claim 18 further comprising the step of opening said generator column to the atmosphere after passing said predetermined quantity of eluant through the column, and drawing sufficient air through the column to leave it damp-dry.

* * * * *

UNITED STATES PATENT AND TRADEMARK OFFICE

CERTIFICATE OF CORRECTION

PATENT NO. : 4,330,507

DATED : May 18, 1982

INVENTOR(S) : Robert L. Lewis

It is certified that error appears in the above-identified patent and that said Letters Patent is hereby corrected as shown below:

Col. 1, line 17, change "99 m" to ---99m---.

Col. 7, line 18, change "Eluate" to ---Eluates---.

Signed and Sealed this

*Fourth* Day of *October 1983*

[SEAL]

*Attest:*

GERALD J. MOSSINGHOFF

*Attesting Officer* *Commissioner of Patents and Trademarks*